United States Patent [19]

Schmierer et al.

[11] Patent Number: 4,747,868
[45] Date of Patent: May 31, 1988

[54] GROWTH-REGULATING, FUNGICIDAL, AND HERBICIDAL CYCLOHEXYLIMIDAZOLE AND CYCLOHEXENYLIMIDAZOLE DERIVATIVES, COMPOSITIONS, AND METHODS OF USE THEREFOR

[75] Inventors: Roland Schmierer, Todtenweis; Hilmar Mildenberger, Kelkheim; Reinhard Handte, Gablingen; Helmut Bürstell, Frankfurt am Main; Burkhard Sachse, Kelkheim; Klaus Bauer, Rodgau; Hermann Bieringer, Eppstein/Taunus, all of Fed. Rep. of Germany

[73] Assignee: Hoechst Aktiengesellschaft, Frankfurt am Main, Fed. Rep. of Germany

[21] Appl. No.: 853,018

[22] Filed: Apr. 17, 1986

[30] Foreign Application Priority Data

Apr. 19, 1985 [DE] Fed. Rep. of Germany ....... 3514116

[51] Int. Cl.⁴ .................. A01N 43/50; A61K 31/415; C07D 231/12
[52] U.S. Cl. ....................................... 71/92; 514/400; 548/343

[58] Field of Search ......................... 548/343; 514/400; 71/92

[56] References Cited

FOREIGN PATENT DOCUMENTS

3217094A1 11/1983 Fed. Rep. of Germany .......... 71/92

Primary Examiner—Henry R. Jiles
Assistant Examiner—J. G. Mullins
Attorney, Agent, or Firm—Curtis, Morris & Safford

[57] ABSTRACT

The new compounds of the formula I or salts thereof

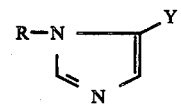

in which R denotes a (substituted) cyclohexyl radical or a (substituted) cyclohexenyl radical; and Y denotes cyano, a (substituted) (di)(thio)carboxylic acid (ester), carboxamide or acetal radical, a keto or oxime radical or a heterocyclic radical, possess an advantageous action as plant growth-regulators and, in addition, have favorable herbicidal and fungicidal properties.

4 Claims, No Drawings

GROWTH-REGULATING, FUNGICIDAL, AND HERBICIDAL CYCLOHEXYLIMIDAZOLE AND CYCLOHEXENYLIMIDAZOLE DERIVATIVES, COMPOSITIONS, AND METHODS OF USE THEREFOR

It is known that 1-phenylimidazole-5-carboxylic acid derivatives, which are described in Patent Applications DE-A No. 3,217,094 and DE-A No. 3,444,918, possess plant growth-regulating properties and, in some cases, herbicidal properties. It has now been found, surprisingly, that, compared with these known compounds, 1-cyclohexylimidazole-5-carboxylic and 1-cyclohexenylimidazole-5-carboxylic acid derivatives possess advantageous plant growth-regulating, herbicidal and fungicidal properties.

The present invention therefore relates to the new compounds of the formula I

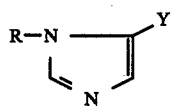   I in which
R denotes a radical of the formulae

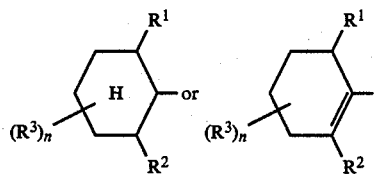

n denotes 0 to 6,
Y denotes

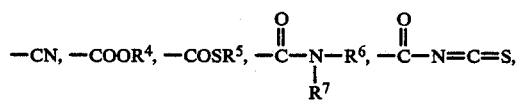

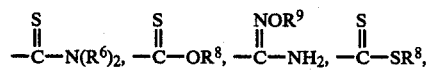

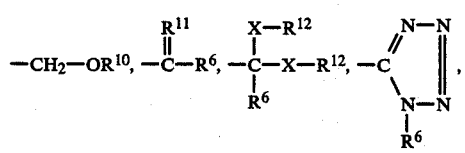

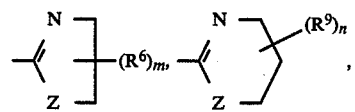

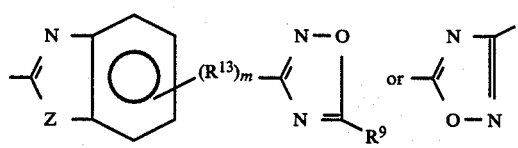

m denotes 1 to 4,
Z denotes O, S or N—$R^6$,

X denotes O or S,
$R^1$ and $R^2$ independently of one another denote ($C_1$–$C_4$)-alkyl or hydrogen,
the $R^3$s independently of one another each denote ($C_1$–$C_4$)-alkyl, ($C_1$–$C_4$)-alkoxy, ($C_1$–$C_4$)-hydroxyalkyl, ($C_1$–$C_4$)-alkoxy-($C_1$–$C_4$)-alkyl or halogen,
$R^4$ denotes hydrogen, ($C_1$–$C_{12}$)-alkyl, ($C_1$–$C_{12}$)-alkyl which is monosubstituted to trisubstituted by hydroxyl, halogen, ($C_1$–$C_6$)-alkoxy, ($C_1$–$C_4$)-alkoxy-($C_1$–$C_4$)-alkoxy, ($C_1$–$C_4$)-alkylthio, ($C_1$–$C_4$)-alkylsulfinyl, ($C_1$–$C_4$)-alkylsulfonyl, mono-($C_1$–$C_4$-alkyl)-amino, di-($C_1$–$C_4$-alkyl)-amino, cyano, aminocarbonyl, ($C_1$–$C_4$)-alkanoyl, ($C_1$–$C_4$-alkoxy)-carbonyl, cyclo-($C_3$–$C_7$)-alkyl, tri-($C_1$–$C_4$-alkyl)silyl, benzyloxy, benzyloxyethoxy, phenyl or phenyl which is mono substituted or polysubstituted by halogen or ($C_1$–$C_4$)-alkyl, by phenoxy or phenylthio both of which can be monosubstituted or polysubstituted by halogen or ($C_1$–$C_4$)-alkyl, by oxiranyl, tetrahydrofuryl, triazolyl, pyridinyl, imidazolyl, carboxyl, carboxylate containing a cation which can be employed in agriculture or by the radical —O—N=C(CH$_3$)$_2$; or $R^4$ denotes ($C_3$–$C_6$)-alkenyl, halogenated ($C_3$–$C_6$)-alkenyl, cyclo-($C_3$–$C_7$)-alkyl which is unsubstituted or substituted by halogen or ($C_1$–$C_4$)-alkyl, cyclo($C_5$–$C_7$)-alkenyl, ($C_3$–$C_6$)-alkynyl, 1,2-epoxyprop-3-yl, phenyl which is unsubstituted or monosubstituted or disubstituted by halogen, nitro, cyano, ($C_1$–$C_4$)-alkyl, ($C_1$–$C_4$alkoxy)-carbonyl or ($C_1$–$C_4$)-alkoxy; ($C_1$–$C_4$-alkyl)-carbonyl, phenylcarbonyl in which the phenyl ring can be substituted by halogen, nitro, cyano or ($C_1$–$C_4$)-alkyl, or a radical of the formulae $R^5$ denotes ($C_1$–$C_{12}$)-alkyl or ($C_1$–$C_{12}$)-alkyl which is not more than disubstituted by ($C_1$–$C_4$)-alkoxyethoxy, cyclo($C_3$–$C_6$)-alkyl, benzyloxy, phenyl, phenoxy, ($C_1$–$C_4$)-alkylthio, ($C_1$–$C_4$-alkoxy)carbonyl, carboxyl or carboxylate containing a cation which can be employed in agriculture,
the $R^6$s independently of one another each denote hydrogen, ($C_1$–$C_6$)-alkyl, phenyl or ($C_3$–$C_6$)-alkenyl,
$R^7$ denotes hydrogen, ($C_1$–$C_{12}$)-alkyl or ($C_1$–$C_{12}$)-alkyl which is not more than disubstituted by ($C_1$–$C_6$)alkoxy, ($C_1$–$C_4$)-alkoxyethoxy, hydroxyl, halogen, cyclo-($C_3$–$C_6$)-alkyl, benzyloxy, cyano, aminocarbonyl, carboxyl, ($C_1$–$C_4$-alkoxy)-carbonyl, formyl, phenyl or phenoxy; phenyl or phenyl which is not more than disubstituted by halogen, nitro, cyano, ($C_1$–$C_4$)-alkyl or ($C_1$–$C_4$)-alkoxy; ($C_3$–$C_6$)-alkenyl, ($C_3$–$C_6$)-cycloalkyl or a radical of the formulae —NR$^6$R$^{17}$, —OR$^9$, —NH—CO—NH$_2$, —NH—CS—NH$_2$ or —SO$_2$R$^{18}$, or
$R^6$ and $R^7$, together with the nitrogen atom to which they are attached, denote a saturated or unsaturated, optionally benzo-condensed three-membered to seven-membered ring which contains up to three heteroatoms belonging to the group comprising O, N or S and is unsubstituted or substituted by $(C_1-C_4)$-alkyl or halogen and can contain a carbonyl group, $R^8$ denotes H, $(C_1-C_6)$-alkyl or phenyl or, in the event that $R = -CS-OR^9$, denotes a cation which can be employed in agriculture, the $R^9$s independently of one another each denote H, $(C_1-C_4)$-alkyl or benzyl;

the $R^{10}$s independently of one another each denote H, $(C_1-C_{12})$-alkyl which is unsubstituted or substituted by phenyl, halogenophenyl, nitrophenyl, cyanophenyl, $(C_1-C_4)$-alkylphenyl, $(C_1-C_4)$-alkoxyphenyl, hydroxyl, cyano, $(C_1-C_4$-alkoxy)carbonyl, $(C_1-C_4)$-alkylthio, $(C_1-C_4)$-alkoxy, cyclo-$(C_5-C_7)$-alkyl or benzyloxy; cyclo-$(C_5-C_8)$-alkyl, $(C_3-C_6)$-alkenyl, halogeno$(C_3-C_6)$-alkenyl, $(C_3-C_6)$-alkynyl, cyclo-$(C_5-C_6)$-alkenyl, $(C_1-C_6$-alkyl)-carbonyl, halogeno-$(C_1-C_6$-alkyl)carbonyl, $[(C_1-C_6$-alkyl)amino]carbonyl, benzoyl, halogenobenzoyl or methylbenzoyl;

$R^{11}$ denotes oxygen (including the bisulfite adducts) or the radical $=N-O-R^{10}$, the $R^{12}$s independently of one another each denote $(C_1-C_6)$-alkyl which is unsubstituted or substituted by phenyl, cyclo-$(C_5-C_7)$-alkyl, $(C_1-C_4)$-alkoxy, $(C_1-C_4)$-alkylthio or halogen; or the two radicals $R^{12}$, together with X and the carbon atom to which they are attached, denote a 5-membered or 6-membered, saturated heterocyclic ring which is unsubstituted or substituted by $(C_1-C_4)$-alkyl, hydroxy-$(C_1-C_4)$-alkyl, halogeno-$(C_1-C_4)$-alkyl or phenyl, the $R^{13}$s independently of one another each denote H, halogen, $(C_1-C_4)$-alkyl, nitro or cyano, the $R^{14}$s and $R^{15}$s independently of one another denote H or $(C_1-C_6)$-alkyl which is unsubstituted or substituted by $(C_1-C_4)$-alkoxy, triazolyl or imidazolyl; cyclo-$(C_3-C_6)$-alkyl, $(C_3-C_6)$-alkenyl, phenyl or benzyl or $R^{14}$ and $R^{15}$, together with the carbon atom to which they are attached, denote cyclo-$(C_5-C_7)$-alkyl which is unsubstituted or substituted by methyl or halogen, $R^{16}$ denotes $(C_1-C_4)$-alkyl, phenyl, $(C_1-C_6$-alkyl)-carbonyl, benzyl, benzoyl, halogenobenzyl, halogenobenzoyl or methylbenzoyl, $R^{17}$ denotes H, $(C_1-C_4)$-alkyl, formyl, $(C_1-C_6$-alkyl)carbonyl, benzoyl, halogenobenzoyl, methylbenzoyl or trihalogenoacetyl and $R^{18}$ denotes $(C_1-C_4)$-alkyl, phenyl or methylphenyl, and to salts and quaternization products thereof which are compatible for agricultural purposes.

The salt formation of quaternization is effected either on a free carboxyl group, for example in the event that $R^4$ or $R^8 = H$, or on the basic nitrogen atom of the imidazole ring. Salt formation or quaternization on the imidazole ring is not possible if $R^4$ or $R^8$ denotes a cation or if $R^4$ or $R^5$ contains a carboxylate group.

The invention embraces all the optical isomers of the compounds of the formula I. These can exist if they contain asymmetrically substituted cycloalkyl or cycloalkenyl rings. The alkyl, alkenyl and alkynyl radicals which appear in the definition of the general formula (I) can be either linear or branched; halogen is to be understood as meaning F, Cl, Br or I, in particular F, Cl or Br.

Halogenated $(C_3-C_6)$-alkenyl contains, in particular, 1 to 3 chlorine or fluorine atoms.

Halogenophenyl, halogenobenzyl or halogenobenzoyl contain, in particular, 1 to 3 fluorine, chlorine or bromine atoms.

Trihalogenoacetyl is to be understood as meaning, in particular, trichloroacetyl and trifluoroacetyl.

Furthermore, preferred compounds of the formula I and salts thereof are those in which R denotes a cyclohexyl radical of the formula

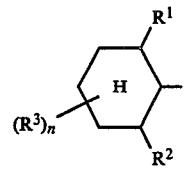

n denotes 0 or 1,
Y denotes

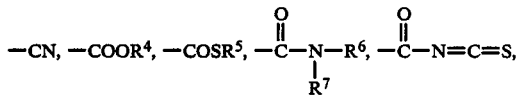

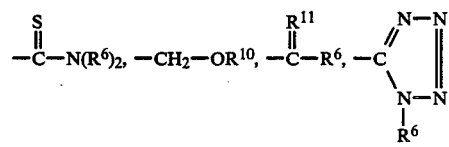

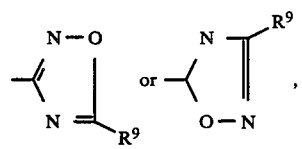

$R^1$ and $R^2$ independently of one another denote $(C_1-C_4)$-alkyl; the $R^3$s each denote $(C_1-C_4)$-alkyl or halogen; $R^4$ denotes hydrogen, $(C_1-C_6)$-alkyl, $(C_1-C_6)$-alkyl which is monosubstituted to trisubstituted by hydroxyl, halogen, $(C_1-C_6)$-alkoxy, $(C_1-C_6)$-alkylthio, $(C_3-C_7)$-cycloalkyl or phenyl, $(C_3-C_6)$-alkenyl, halogenated $(C_3-C_6)$-alkenyl, cyclo-$(C_3-C_6)$-alkyl, $(C_3-C_6)$-alkynyl, phenyl or a radical of the formulae

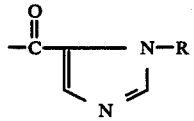

or $-N=CR^{14}R^{15}$; $R^5$ denotes $(C_1-C_4)$-alkyl; $R^6$ denotes hydrogen, $(C_1-C_4)$-alkyl, phenyl or allyl; $R^7$ denotes hydrogen, $(C_1-C_{12})$-alkyl or $(C_1-C_{12})$-alkyl which is not more than disubstituted by $(C_1-C_6)$-alkoxy, hydroxyl, halogen, cyclo-$(C_3-C_6)$-alkyl, benzyloxy, cyano, aminocarbonyl, carboxyl, $(C_1-C_4$-alkoxy)-carbonyl or formyl, phenyl or phenyl which is not more than disubstituted by halogen, nitro, cyano, $(C_1-C_4)$-alkyl or $(C_1-C_4)$-alkoxy; allyl, $(C_3-C_6)$-cycloalkyl, a radical of the formulae $-NR^6R^{17}$ or $OR^9$, or $R^6$ and $R^7$, together with the nitrogen atom, form a heterocyclic ring of the formulae

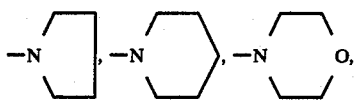

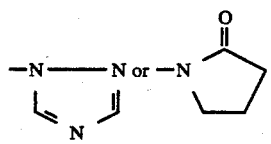

$R^9$ denotes H or $(C_1-C_4)$-alkyl,
$R^{10}$ denotes hydrogen, $R^{11}$ denotes oxygen (including the bisulfite adducts) or the radical $=N-O-R^{10}$,
$R^{14}$ and $R^{15}$ denote unsubstituted $(C_1-C_4)$-alkyl, or
$R^{14}$ and $R^{15}$, together with the carbon atom to which they are attached, denote cyclo-$(C_5-C_7)$-alkyl and
$R^{17}$ denotes H, $(C_1-C_4)$-alkyl or formyl.

In the event that further basic nitrogen atoms—in addition the imidazole ring—are found in the substituents mentioned, multiple salt formation or quaternization is also possible.

Acids suitable for the salts are any inorganic or organic acids capable by virtue of their pK value of forming salts, for example hydrogen halide acids, nitric acid, sulfuric acid, phosphoric acid, phosphonic acids, sulfonic acids, halogenoacetic acids or oxalic acid.

Quaternization products are to be understood as meaning the reaction products with alkyl halides, alkylthioalkyl halides, alkoxyalkyl halides, especially $(C_1-C_6)$-alkyl halides and phenacyl halides which are optionally substituted, in particular halogenated, in the phenyl radical. The preparation of the quaternization products of the compounds of the formula I is effected by methods which are generally customary.

Suitable cations for $R^4$, $R^8$ or $R^5$ which can be employed in agriculture are metal cations, for example alkali and alkaline earth metal cations, such as Na, K or Mg, or organic cations, such as ammonium having organic substituents, phosphonium, sulfonium or sulfoxonium having organic substituents, or other nitrogen cations.

Ammonium having organic substituents denotes primary, secondary, tertiary, quaternary, aliphatic, aromatic or heteroaromatic ammonium which can contain 1 to three N atoms. The nitrogen atoms of the amine can in this case also be part of a cyclic system. The following may be mentioned as examples of such ammonium salts: mono-, di-, tri- or tetra-$[(C_1-C_6)$-alkyl]-ammonium, such as isopropylammonium, butylammonium, stearylammonium or triethylammonium, mono-, di- or tri-$[(C_1-C_4)$-alkoxy-$(C_1-C_4)$-alkyl]-ammonium or mono-, di- or tri-$[(C_1-C_6)$-alkanol]-ammonium, such as methoxyethylammonium, methoxypropylammonium, triethanolammonium or tripropanolammonium, or ammonium compounds containing mixed radicals, such as tert.-butyldiethanolammonium, triethylbenzylammonium, hydroxyethyltrimethylammonium or chloroethyltrimethylammonium; or allylammonium, diallylammonium, cyclohexylammonium, menthylammonium, aminoethylammonium, ethylenediammonium, benzhydrylammonium, pyrrolidinium, morpholinium, 3-pyridylammonium, piperidinium or piperazinium, or an ammonium derived from an amino acid or an ester thereof, such as $NH_3-CH_2-COOCH_3$.

Correspondingly, phosphonium having organic substituents, organic sulfonium or organic sulfoxonium contain aliphatic or arylaliphatic radicals.

Examples of other nitrogen cations are hydrazonium, hydroxylammonium, guanidinium, aminoguanidinium or substitution products thereof.

The invention also relates to a process for the preparation of the compounds of the formula I and salts or quaternization products thereof, wherein
(a) a bisformyl ester of the formulae IIa or IIb

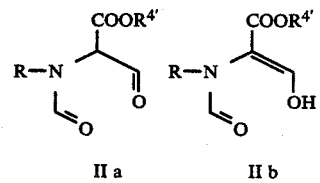

in which $R^{4'}$ denotes $(C_1-C_{12})$-alkyl, $(a_1)$ is cyclized by means of a $(C_1-C_3)$-carboxamide or $(a_2)$ is reacted with potassium thiocyanate to give a 2-mercaptoimidazole derivative and this is desulfurized with nitric acid and sodium nitrite, or
(b) a phenylimidazole derivative of the formula III

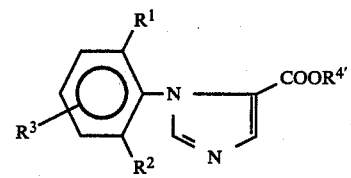

is partially or completely hydrogenated in the phenyl ring, and derivatives are prepared from the compounds obtained under (a) or (b).

In forming derivatives, the radical $-COOR^4$ is modified in a known manner, for example by saponification, esterification, transesterification, amidation, salt formation, reduction or oximation, as described, for example, in Patent Applications DE-A No. 3,444,918 and DE-A No. 3,442,690, or salt formation or quaternization is carried out at the basic nitrogen atom of the imidazole ring.

In process (a) it is preferable to employ formamide as the carboxamide. It is preferably reacted in the presence of mineral acid in molar amounts at 50°-200° C., in particular 100°-170° C.

The bisformyl compounds of the formula IIa or IIb can be prepared readily by known processes (German Offenlegungsschrift No. 3,217,094) from 2,6-dialkylcyclohexylamines (German Offenlegungsschrift No. 3,123,731) or 2,6-dialkylcyclohexenylamines (U.S. Pat. No. 4,351,667).

The phenylimidazole compounds III are also known from the literature (DE-A No. 3,217,094). Catalysts which can be used for the hydrogenation are noble metal hydrogenation catalysts, such as, for example, platinum, palladium or rhodium catalysts. The reactions can be carried out in the presence of solvents, such as tetrahydrofuran, ethanol, methanol or ethyl acetate, advantageously under pressure, at temperatures of 0°-200° C., in particular 20°-150° C.

The salts of the compounds of the formula (I) can be obtained in a simple manner by customary methods of forming salts, for example by dissolving a compound of the formula (I) in a suitable organic solvent and adding the acid, and they can be isolated in a known manner, for example by filtration, and can, if necessary, be purified by washing with an inert organic solvent.

By means of the compounds according to the invention it is possible to achieve typical growth-regulating effects which—compared with the compounds disclosed in DE-A No. 3,217,094—can be employed in various crops, even at low dosages. They intervene in a regulatory manner in the internal metabolism of the plant and can thus be employed for selectively influencing the constituents of plants and for facilitating harvesting and for initiating desiccation and inhibition of growth. Furthermore, they are suitable for the general control and inhibition of undesired vegetative growth, without thereby destroying the plants. In many monocotyledonous and dicotyledonous crops inhibition of vegetative growth is very important, since it is possible by this means to reduce or completely prevent lodging. The growth-regulatory effectiveness of the compounds as growth inhibitors in cereals, corn, soya, tobacco, cotton, field beans, rape, rice and lawns should be singled out particularly, as should their capacity to increase the content of desirable constituents, such as carbohydrates (for example sugarcane or millet crops) and protein in useful plants. Finally, the compounds exhibit a very good improvement in the abscission of fruit, particularly in the case of citrus fruit.

In addition, the compounds, according to the invention, of the formula I possess an excellent herbicidal effectiveness against a broad spectrum of economically important monocotyledonous or dicotyledonous weeds. Even perennial weeds which sprout from rhizomes, root-stocks or other long-life organs and which are difficult to combat are satisfactorily controlled by the active compounds. In this respect it is immaterial whether the substances are applied by the presowing, preemergence or postemergence technique.

If the compounds according to the invention are applied to the surface of the soil before germination, either the emergence of the weed seedlings is completely prevented or the weeds grow until they reach the cotyledonous stage, but then suspend growth and finally die completely after a period of three to four weeks.

If the active compounds are applied to the green parts of plants by the postemergence technique, a drastic cessation of growth also takes place very quickly after the treatment, and the weed plants remain in the stage of growth existing at the time of application or die off at varying rates after a certain time, so that competition by weeds, harmful to a crop plant, can be eliminated in this manner very soon and with lasting effect by using the new agents according to the invention.

Although the compounds according to the invention display an excellent herbicidal activity against monocotyledonous or dicotyledonous weeds, crop plants of economically important crops such as, for example, wheat, barley, rye, rice, maize, sugar beet, cotton and soya, are damaged only insubstantially, or not at all. For these reasons, the present compounds are very suitable for selectively combating undesirable plant growth in useful agricultural plants.

A particularly good herbicidal effectiveness is achieved if the compounds according to the invention are employed in the cultivation of water rice. Under these conditions they display a broad action against a series of rice weeds, such as, for example, species belonging to the group of the Cyperaceae, for example Eleocharis, Cyperus or Scirpus, or species such as Sagittaria, Pistia, dicotyledonous weeds and, particularly, also grasses, such as *Echinochloa crus galli*.

The compounds according to the invention are completely tolerated by the crop plant rice, so that these compounds can be employed for selectively combating weeds in rice by the preemergence and postemergence technique.

The compounds according to the invention are particularly distinguished by the fact that they combat, in very effective and at low application rates, numerous seed-propagated weeds and also weeds which germinate from long-life organs, such as tubers or rhizomes, and are difficult to combat, and they do not damage the rice at all.

The compounds, according to the invention, of the formula I are also distinguished by an excellent fungicidal action. Fungal pathogens which have already penetrated into the plant tissue can be combated successfully in a curative manner. This is particularly important and advantageous in the case of fungal diseases which can no longer be combated effectively by means of the generally customary fungicides after infection has taken place. The spectrum of action of the compounds claimed includes a large number of different phytopathogenic fungi or economic importance, such as, for example, *Piricularia oryzae, Pellicularia sasakii*, various species of rust, *Venturia inaequalis*, Cercospora species and powdery mildew fungi in the cultivation of fruit, vegetables, cereals and ornamental plants, *Botrytis cinerea, Pseudocercosporella herpotrichoides*, Fusarium species and some of the fungi included under the phycomycetes, such as, for example, *Plasmopara viticola* and *Pseudoperonospora cubensis*.

The compounds of the formula I are also suitable for use in industrial fields, for example as wood preservatives, as preservatives in paints and cooling lubricants for metal machining or as preservatives in drilling and cutting oils.

The agents can be used in the customary formulations as wettable powders, emulsifiable concentrates, atomizable solutions, dusting agents, addressing agents, dispersions, granules or microgranules.

The application also relates to plant protection agents distinguished by an effective content of at least one compound of the general formula (I).

When used for practical purposes, the compounds according to the invention can, if appropriate, also be combined advantageously with known growth regulators. Known growth regulators of this type are the compounds of the formula

in which R denotes OH or Cl (common name chlormequat for RA=Cl), and also N,N-dimethylpiperidinium chloride (V, mepiquat, chloride), α-cyclopropyl-4-methoxy-α-(pyrimidin-5-yl)-benzyl alcohol (VI, ancymidol), (3aα, 4β, 4aα, 6aα, 7β, 7aα)-1-(4-chlorophenyl)-3a, 4, 4a, 6a, 7, 7a-hexahydro-4,7-methano-1H-[1,2]diazeto[3,4-f]benzotriazole (VII, tetcylacis), succinic acid mono-2,2-dimethylhydrazide (VIII, diaminoazide), 6-hydroxy-2H-pyridazin-3-one (IX, maleic acid hydrazide), 2-chloro-9-hydroxy-9H-fluorene-9-carboxylic acid (X, chlorflurenol), 5'-(trifluoromethanesulfonamido)-acetate-2',4'-xylidide (XI, mefluidide) and 2-chloroethylphosphonic acid (XII, ethephon).

The growth-regulating effects of the compounds of the formulae (IV) to (XII) are described in the Plant Growth Regulator Handbook of the Plant Growth Regulator Working Group, 2nd edition 1981.

Instead of the compounds of the formulae (VI) and (V), it is also possible, in principle, to employ comparable salts containing another customary anion, such as bromide, nitrate or ½ sulfate, instead of the chloride ion.

Surprisingly, striking synergistic effects were found when the compounds of the formula (I) were combined with the compounds of the formulae (IV) to (XII). Thus the desired effects can be achieved by employing these combinations at lower dosages than would have been expected from the action of the individual components. The combinations also make it possible to reduce wild growth phenomena, so that the combinations can also be employed in conservation of the landscape. Furthermore, the compounds are excellently suitable for the general control and inhibition of undesired vegetative growth, such as the formation of sideshoots, without destroying the plants. The compounds of the formula (I) can also be advantageously combined together with two different compounds of the formulae (IV) to (XII).

The ratios in which the components of the general formula (I) are mixed with the compounds of the formulae (IV) to (XII) can vary within wide limits, for instance between 250:1 and 1:10. The choice of mixing ratio depends on the nature of the mixing partner, the stage of development of the plants and the extent of the growth-regulatory action desired. It is preferable to select mixing ratios from 10:1 to 1:10.

The combinations can either be in the form of mixed formulations of the components, which are then used in a customary manner, diluted with water; or they can be prepared in the form of so-called tank mixtures by jointly diluting with water the separately formulated components; it is also possible to use the components successively, i.e. the components are then applied in individual formulations.

The compounds of the general formula (I) can also be combined with natural or plant hormones, such as auxins or cytokinins.

The compounds, according to the invention, of the general formula (I), if appropriate mixed with further active components, such as the compounds of the formulae IV to XII, can be used in the customary formulations as wettable powders, emulsifiable concentrates, atomizable solutions, dusting agents, dressing agents, dispersions, granules or microgranules.

Wettable powders are preparations which are uniformly dispersible in water and, in addition to the active compound(s), also contain, besides, if appropriate, a diluent or inert substance, wetting agents, such as polyoxethylated fatty alcohols, alkylsulfonates or alkylphenylsulfonates, and/or dispersing auxiliaries, such as sodium ligninsulfonate, sodium 2,2'-dinaphthylmethane-6,6'-disulfonate, sodium dibutylnaphthalenesulfonate or sodium oleoylmethyltauride. The preparation is effected in a customary manner, for example by grinding and mixing the components.

Emulsifiable concentrates can be prepared, for example, by dissolving the active compound(s) in an inert organic solvent, such as butanol, cyclohexanone, dimethylformamide, xylene or fairly high-boiling aromatic hydrocarbons or aliphatic or cycloaliphatic hydrocarbons, with the addition of one or more emulsifiers. In the case of liquid active compounds, the solvent component can also be wholly or partly omitted. The following, for example, can be used as the emulsifiers: calcium alkylarylsulfonates, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, fatty alcohol/propylene oxide condensation products, alkyl polyglycol ethers, sorbitan fatty acid esters, polyoxethylenesorbitan fatty acid esters or polyoxethylenesorbitol esters.

Dusting agents can be obtained by grinding the active compound(s) with finely divided, solid materials, for example talc, natural clays, such as kaolin, bentonite or pyrophillite, or diatomaceous earth. Granules can be prepared either by atomizing the active compound(s) onto an adsorptive, granulated inert material or by applying concentrations of active compound to the surface of carriers such as sand, kaolinite or granulated inert material by means of binders, for example polyvinyl alcohol, sodium polyacrylate or mineral oils. It is also possible to granulate suitable active compounds—if desired with fertilizers—in the manner customary for the preparation of fertilizer granules.

The concentration of active compound in wettable powders is about 10 to 90% by weight; the remainder up to 100% by weight is composed of customary formulation ingredients. In emulsifiable concentrates the concentration of active compound can be about 5 to 80% by weight. Formulations in the form of dusts contain in most cases 0.5 to 20% by weight of active compound(s); atomizable solutions contain about 2 to 20% by weight. In the case of granules, the content of active compound depends in part on whether the active compound is in a liquid or solid state and on the granulating auxiliaries, fillers and the like which are used. In addition, the said active compound formulations contain, if appropriate, the tackifiers, wetting agents, dispersing agents, emulsifiers, penetration agents, solvents, fillers or carriers which are customary in a particular case.

For application, the concentrates available in a commercial form are, if appropriate, diluted in a customary manner, for example with water in the case of wettable powders, emulsifiable concentrates, dispersions and, in part, also in the case of microgranules. Formulations in the form of dusts and granules and atomizable solutions are usually not diluted further with other inert materials before application.

The application rates of the active compounds of the formula I can vary within wide limits, depending on the indication. When used as plant growth-regulators or as fungicides, they are generally between 0.02 and 1.5 kg of active compound per hectare. In the event of use as herbicides, they preferably vary between 0.05 and 3.0 kg of active compound per hectare.

FORMULATION EXAMPLES

Example 1

A dusting agent is obtained (a) by mixing 10 parts by weight of active compound(s) and 90 parts by weight of talc or another inert material and comminuting the mixture in a hammer mill, or (b) by homogenizing in the same manner 60 parts by weight of active compound, 35 parts by weight of talc and 5 parts by weight of tackifier (for example a polysaccharide such as ®Rhodopol made by Rhone-Poulenc S.A.).

Example 2

A wettable powder which is readily dispersible in water is obtained by mixing 25 parts by weight of active compound(s), 64 parts by weight of kaolin-containing quartz as an inert material, 10 parts by weight of potassium ligninsulfonate and 1 part by weight of sodium oleoylmethyltauride as a wetting and dispersing auxiliary, and grinding the mixture in a pinned disk mill. A formulation containing 5% of active compound can have the following composition: 5% of active compound(s), 6% of a sulfonated naphthalene/formaldehyde condensation product (for example ®Dispersogen A made by Hoechst AG), 2% of an Na salt of an alkylnaphthalenesulfonic acid (for example ®Leonil DB made by Hoechst AG), 5% of a mixture of polypropylene glycol and SiO2 (for example ®Acrotin 341 made by Hoechst AG), 25% of a grade of SiO2 (for example ®Sipernat made by Degussa AG) and 57% of kaolin, grade 1777.

Example 3

A dispersion concentrate which is readily dispersible in water is obtained by mixing 20 parts by weight of active compound(s) with 6 parts by weight of an alkylphenol polyglycol ether (for example ®Triton X 207 made by Rohm and Haas Co.), 3 parts by weight of isotridecanol polyglycol ether (8 units of ethylene oxide) and 71 parts by weight of paraffinic mineral oil (boiling range approx. 255° to over 377° C.) and grinding the mixture in a ball mill to a fineness of less than 5 μm.

Example 4

An emulsifiable concentrate is obtained from 15 parts by weight of active compound(s), 75 parts by weight of cyclohexanone as solvent and 10 parts by weight of oxyethylated nonylphenol (10 units of ethylene oxide) as emulsifier.

CHEMICAL EXAMPLES

Example 1

Ethyl 1-(2,6-diethylcyclohexyl)-imidazole-5-carboxylate 39.7 g (0.13 mol) of ethyl 2-(N-formyl-2,6-diethylcyclohexylamino)-3-hydroxy-acrylate, together with 240 ml of formamide and 24 ml of concentrated hydrochloric acid, were heated at 150° C. for 6 hours. After cooling, the mixture was extracted twice with diisopropyl ether, the organic phase was washed twice with water, dried over sodium sulfate and evaporated, and the residue was chromatographed over a silica gel column (mobile phase 7:3 petroleum ether (low-boiling)/ethyl acetate). 20.5 g (55% of theory) of ethyl 1-(2,6-diethylcyclohexyl)-imidazole-5-carboxylate was obtained as a colorless oil. Identification was effected by means of NMR spectroscopy.

Example 2

Methyl 1-(2,6-dimethylcyclohexyl)-imidazole-5-carboxylate

A solution of 19.4 g (0.20 mol) of potassium thiocyanate in 100 ml of water was added to 29.7 g (0.10 mol) of methyl 2-(N-formyl-2,6-dimethylcyclohexylamine)-3-hydroxyacrylate in 200 ml of tetrahydrofuran. After 22 g of concentrated hydrochloric acid had been added dropwise, the mixture was heated at 60° C. for 12 hours. After cooling, the organic phase was separated off and evaporated. The residue was taken up in 50 ml of methylene chloride, and this solution was added dropwise, at 35° C. and under a nitrogen atmosphere, to a solution of 200 ml of 15% strength nitric acid, 200 ml of methylene chloride and 5 g of sodium nitrite. Stirring was continued for a further hour at 35° C., the mixture was cooled to 0°–5° C. and the nitrate was filtered off with suction. In order to liberate the imidazole, the nitrate was suspended in methylene chloride and neutralized with 1N sodium hydroxide solution. Drying and evaporating the organic phase gave 18.3 g (66% of theory) of methyl 1-(2,6-dimethylcyclohexyl)-imidazole-5-carboxylate as a colorless oil. Identification was effected by NMR spectroscopy.

The compounds which follow can be prepared by the processes described above. Where X in Tables I and II represent radicals other than —COOCH3 or COOC2H5, these compounds were prepared from the corresponding esters by customary processes which are generally known.

TABLE I

Cyclohexyl derivatives

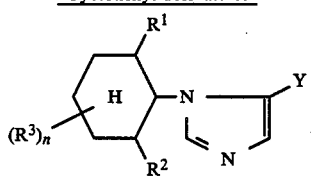

| Example No. | $R^1$ | $R^2$ | $(R^3)_n$ | Y | m.p. (°C.)/ b.p. (°C.) |
|---|---|---|---|---|---|
| 3 | CH(CH3)2 | CH(CH3)2 | H | —COO.½Zn | |
| 4 | CH3 | CH3 | " | —COOH | 185–91 |
| 5 | " | " | " | —COOCH2—COOCH3 | oil |
| 6 | " | " | " | —CON⟨O⟩ | 93–8 |
| 7 | " | " | " | —C(=S)—NH2 | |
| 8 | " | " | 4-CH3 | —CHO | oil |
| 9 | " | " | " | —CH(OC2H5)2 | oil |

TABLE I-continued
Cyclohexyl derivatives

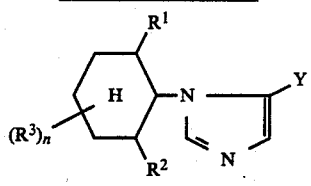

| Example No. | R¹ | R² | (R³)ₙ | Y | m.p. (°C.)/ b.p. (°C.) |
|---|---|---|---|---|---|
| 10 | " | " | " | —CH₂—OH | |
| 11 | " | " | 4-OCH₃ | —COO—CH₂—S—CH₃ | |
| 12 | " | C₂H₅ | H | —COOH | |
| 13 | " | " | " | ![structure: —C(=N-O-N=)C(CH₃)] | 213–6 |
| 14 | " | " | " | —C(NH₂)=N—OH | |
| 15 | " | " | " | —C≡N | oil |
| 16 | " | " | " | —C(=N—O—)C(CH₃) (isoxazoline) | oil |
| 17 | C₂H₅ | " | " | —COOH | 170–4 |
| 18 | " | " | " | —COOH.NH₃ | 198 (decomp.) |
| 19 | " | " | " | —COONa | >240 (decomp.) |
| 20 | " | " | " | —COOK | >220 (decomp.) |
| 21 | " | " | " | —COOH.H₂N—(CH₂)₃—O—CH₃ | 107–11 |
| 22 | " | " | " | —COOH.N(—CH₂—CH₂—OH)₃ | resin |
| 23 | " | " | " | —COOH.H₂N—CH₂—COOCH₃ | resin |
| 24 | " | " | " | —COOH.HN(piperidine) | resin |
| 25 | " | " | " | —COOH.H₂N—NH—C(=O)—NH₂ | 152–8 |
| 26 | " | " | " | —COOH (Hydrochloride) | >205 (decomp.) |
| 27 | " | " | " | —COOH (Nitrat) | >188 (decomp.) |
| 28 | " | " | " | —COOH (2-Chloroethylphosphonate) | 102–5 |
| 29 | " | " | " | —COOCH₃ | Öl |
| 30 | " | " | " | —COOCH(CH₃)₂ | Öl |
| 31 | " | " | " | —COO—N=C(CH₃)₂ | Öl |
| 32 | " | " | " | —C(=S)—OC₂H₅ | Öl |
| 33 | " | " | 4-Br | —COOH | |
| 34 | " | " | " | —COOH.HN(morpholine) | |
| 35 | " | —CH(CH₃)₂ | H | —COOH | 142–9 |
| 36 | " | " | " | —CN | |
| 37 | " | " | " | —COCH₃ | |

TABLE I-continued
Cyclohexyl derivatives

[Structure: cyclohexyl ring with R¹, R², (R³)ₙ substituents, H, connected via N to imidazole ring bearing Y]

| Example No. | R¹ | R² | (R³)ₙ | Y | m.p. (°C.)/ b.p. (°C.) |
|---|---|---|---|---|---|
| 38 | " | " | " | —CH=NOH | |
| 39 | " | " | " | —C(=O)—S—$C_2H_5$ | |
| 40 | " | " | " | —COOPhenyl | |
| 41 | " | " | " | —$CONH_2$ | oil |
| 42 | " | " | " | —C(=O)—NH—OH | |
| 43 | " | " | " | —C(=O)NH—$NH_2$ | |
| 44 | " | " | " | —C(=O)NH—N($CH_3$)$_2$ | |
| 45 | " | " | " | [oxazoline: —C(=N)—O—] | |
| 46 | " | " | " | [dimethyloxazoline: —C(=N)—O—C($CH_3$)$_2$] | |
| 47 | " | " | " | —COO—$CH_2$—CN | |
| 48 | " | " | " | —COO—$CH_2$—$COOCH_3$ | |
| 49 | $CH_3$ | $C_2H_5$ | " | —$COOCH_3$ | oil |
| 50 | " | " | " | —$COOC_2H_5$ | oil |
| 51 | " | " | " | —COOH.N(—$CH_2$—$CH_2$—OH)$_3$ | resin |
| 52 | " | " | " | —COOH.N(piperidine) | resin |
| 53 | $C_2H_5$ | " | " | —$CONH_2$ | oil |
| 54 | " | " | " | —C≡N | oil |
| 55 | " | " | " | —C(=NOH)$NH_2$ | 127–133 |
| 56 | " | " | " | —COO—$CH_2$—CH=$CH_2$ | oil |
| 57 | " | " | " | —COO—$CH_2$—CH=$CH_2$ (Hydrochloride) | 125–130 |
| 58 | " | " | " | —COO—$CH_2$—$CCl_3$ | oil |
| 59 | " | " | " | —CONH—$CH_2$—CH($OCH_3$)$_2$ | 42–45 |
| 60 | " | " | " | —CONH—$CH_2$—CHO | oil |
| 61 | " | " | " | —C(=O)—NHOH | resin |
| 62 | " | " | " | —C(=S)—$NH_2$ | 112–115 |
| 63 | " | " | " | —COO—N=C($CH_3$)$_2$ (Hydrochloride) | resin |
| 64 | " | " | " | —CONH—$CH_3$ | oil |
| 65 | " | " | " | —CONH—CH($CH_3$)$_2$ | oil |
| 66 | " | " | " | —CON(piperidine) | oil |
| 67 | " | " | " | —$CH_2$OH | oil |
| 68 | " | " | " | —CHO | oil |
| 69 | " | " | " | —CHNOH | oil |
| 70 | " | " | " | —C(=O)—$NHOCH_3$ | oil |
| 71 | " | " | " | —COO—CH($CH_3$)—n-$C_6H_{13}$ | oil |
| 72 | " | " | " | —COO—C(=O)— [linked to imidazole-N-cyclohexyl bearing 2,6-diethyl substituents] | 98–101 |

TABLE I-continued
Cyclohexyl derivatives

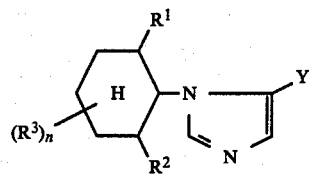

| Example No. | R¹ | R² | $(R^3)_n$ | Y | m.p. (°C.)/ b.p. (°C.) |
|---|---|---|---|---|---|
| 73 | " | " | " | $-\overset{\overset{O}{\|}}{C}-N=C=S$ | oil |
| 74 | " | " | " | $-CON(C_2H_5)_2$ | |
| 75 | " | " | " | $-CO-N(CH_3)Phenyl$ | |
| 76 | " | " | " | $-CO-N(Cyclohexyl)-i-C_3H_7$ | |
| 77 | " | " | " | $-CON(CH_2-CH=CH_2)_2$ | |
| 78 | " | " | " | $-CONH(C_9H_{19})$ | |
| 79 | " | " | " | $-CONH-CH_2-cyclohexyl$ | |
| 80 | " | " | " | CONH—△ | |
| 81 | " | " | " | $-CO-N\underset{N}{\overset{\diagup N=\diagdown}{\underset{\diagdown}{\diagup}}}$ | |

TABLE II
Cyclohexenyl derivatives

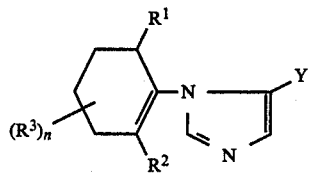

| Example No. | R¹ | R² | $(R^3)_n$ | Y | m.p. (°C.)/b.p. (°C.) |
|---|---|---|---|---|---|
| 82 | $CH_3$ | $CH_3$ | H | COOH | |
| 83 | " | " | " | $COOH.\frac{1}{2}(H_2N-CH_2-CH_2-NH_2)$ | |
| 84 | " | " | " | $COOCH_3$ | |
| 85 | " | " | " | $COOCH_2-CH=CH_2$ | |
| 86 | $C_2H_5$ | $C_2H_5$ | " | COOH | |
| 87 | " | " | " | $-COO-Cyclohexyl$ | |
| 88 | " | " | " | $-CONH-CH_2-CH_2-OH$ | |
| 89 | " | " | " | $-\underset{NH-N}{\overset{N-N}{C\diagdown\diagup}}$ | |
| 90 | $CH(CH_3)_2$ | $CH(CH_3)_2$ | " | COOH | |
| 91 | " | " | " | COOLi | |
| 92 | " | " | " | $COO.\frac{1}{2}Mg$ | |
| 93 | " | " | " | $-COO-N\underset{\text{phthalimide}}{}$ | |

TABLE II-continued

Cyclohexenyl derivatives

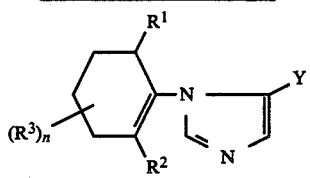

| Example No. | R¹ | R² | (R³)ₙ | Y | m.p. (°C.)/b.p. (°C.) |
|---|---|---|---|---|---|
| 94 | " | " | " | ![structure: -C(=O)-N-N with O bridge forming a ring with N] | — |
| 95 | " | " | " | $-COOCH_2-CF_3$ | |

BIOLOGICAL EXAMPLES

A. Growth Regulation

I. Inhibition of growth in wheat

Young cereal plants (wheat, barley and rye) in the 3-leaf stage were sprayed until they were dripping wet with compounds according to the invention in various concentrations of active compound (kg/hectare), in tray tests in a greenhouse.

When the untreated control plants had reached a height of growth of about 55 cm, the growth of all the plants was measured and the inhibition of growth was calculated as a % of the growth of the control plants. In addition, the phytotoxic action of the compound was observed. The inhibition of growth was determined as a percentage figure, 100% denoting cessation of growth and 0% denoting growth similar to that of the untreated control plants. It was found that the compounds have very good growth-regulating properties. The results are summarized in Table III.

II. Inhibition of growth in water rice

Rice plants were cultivated and, in the stage of maximum tillering, were treated with compounds according to the invention. The substances were both applied by spraying and put into the water.

3 weeks after the treatment, the growth of all the plants was measured and the inhibition of growth was calculated as a % of the growth of the control plants. Attention was also paid to possible phytotoxic action of the compounds.

The inhibition of growth was determined as a percentage figure, 100% denoting cessation of growth and 0% denoting growth similar to that of the untreated control plants. It was found that the compounds have very good growth-regulating properties. The results are summarized in Table III.

III. Inhibition of growth in soybeans

Soybeans approx. 10 cm high were sprayed with the active compound formulations until they were dripping wet. Assessment was carried out after 3 weeks.

The inhibition of growth was determined as a percentage figure, 100% denoting cessation of growth and 0% denoting growth similar to that of the untreated control plants. It was found that the compounds have very good growth-regulating properties. The results are summarized in Table III below.

TABLE III

| Compound according to Example No. | Application concentration (kg/ha) | Inhibition of growth as % in | | | | |
|---|---|---|---|---|---|---|
| | | Rice | Wheat | Barley | Rye | Soya |
| 1 | 1.0 | 14 | 12 | 10 | 11 | 9 |
| | 0.75 | 9 | 9 | 8 | 7 | 6 |
| 2 | 1.0 | 12 | 12 | 11 | 10 | 9 |
| | 0.75 | 9 | 9 | 8 | 7 | 6 |
| 4 | 1.0 | 18 | 11 | 11 | 10 | 11 |
| | 0,75 | 11 | 9 | 8 | 9 | 9 |
| 8 | 1.0 | 11 | 12 | 10 | 11 | 9 |
| | 0,75 | 7 | 7 | 7 | 8 | 8 |
| 12 | 1.0 | 19 | 12 | 11 | 12 | 10 |
| | 0,75 | 17 | 10 | 9 | 9 | 8 |
| 13 | 1.0 | 12 | 10 | 11 | 11 | 12 |
| | 0,75 | 8 | 8 | 9 | 9 | 8 |
| 16 | 1.0 | 13 | 11 | 11 | 12 | 11 |
| | 0,75 | 7 | 8 | 8 | 8 | 9 |
| 17 | 1,0 | 19 | 12 | 11 | 11 | 11 |
| | 0,75 | 17 | 11 | 8 | 9 | 9 |
| 18 | 1.0 | 18 | 12 | 12 | 12 | 11 |
| | 0.75 | 17 | 11 | 8 | 9 | 7 |
| 19 | 1.0 | 22 | 13 | 12 | 9 | 12 |
| | 0.75 | 17 | 10 | 10 | 7 | 7 |
| 21 | 1.0 | 19 | 12 | 10 | 12 | 11 |
| | 0.75 | 17 | 11 | 10 | 9 | 7 |
| 22 | 1.0 | 23 | 14 | 13 | 12 | 9 |
| | 0.75 | 20 | 7 | 7 | 8 | 7 |
| 24 | 1.0 | 18 | 12 | 12 | 13 | 12 |
| | 0.75 | 16 | 9 | 10 | 11 | 8 |
| 26 | 1.0 | 20 | 14 | 12 | 13 | 9 |
| | 0.75 | 18 | 9 | 9 | 9 | 9 |
| 28 | 1,0 | 17 | 13 | 14 | 20 | 12 |
| | 0.75 | 16 | 10 | 9 | 9 | 7 |
| 29 | 1.0 | 13 | 12 | 11 | 13 | 12 |
| | 0,75 | 10 | 7 | 8 | 9 | 11 |
| 30 | 1,0 | 13 | 12 | 12 | 11 | 13 |
| | 0.75 | 9 | 7 | 8 | 9 | 7 |
| 31 | 1.0 | 23 | 14 | 14 | 13 | 13 |
| | 0,75 | 20 | 13 | 9 | 10 | 10 |
| 33 | 1.0 | 22 | 16 | 16 | 14 | 12 |
| | 0.75 | 20 | 12 | 10 | 10 | 10 |
| 41 | 1.0 | 14 | 12 | 12 | 13 | 13 |
| | 0.75 | 9 | 11 | 10 | 9 | 8 |
| 42 | 1.0 | 15 | 13 | 12 | 12 | 13 |
| | 0.75 | 11 | 10 | 9 | 9 | 7 |

Phytotoxic effects were not observed for any of the compounds tested.

B. Herbicidal Action

The damage caused to weed plants and the tolerance by crop plants were assessed in terms of a code in which the effectiveness is expressed in numerical values from 0 to 5. These denote as follows:

0=no action or damage

1=0-20% action or damage
2=20-40% action or damage
3=40-60% action or damage
4=60-80% action or damage
5=80-100% action or damage IV. Action on weeds by the preemergence technique Seeds or pieces of rhizome of monocotyldenous and dicotyledonous weed plants were laid out in sandy loam soil in plastics pots (diameter 9 cm), and were covered with soil. The compounds according to the invention, formulated in the form of wettable powders or emulsion concentrates, were then applied to the surface of the covering soil at various dosages in the form of aqueous suspensions or emulsions, at a water application rate equivalent to 600-800 liter/hectare. After the treatment, the pots were placed in a greenhouse and were kept under good growth conditions for the weeds (temperature: 23 plus/minus 2° C.; relative humidity: 60-80%). Visual assessment of the damage to the plants or to their emergence was carried out in comparison with untreated controls when the test plants had emerged after a test time of 3-4 weeks. As the assessment figures in Table IV show, the compounds according to the invention have a good herbicidal preemergence effectiveness against a broad spectrum of grass-like weeds and weeds.

TABLE IV

Herbicidal effect of the compounds according to the invention by the preemergence technique

| Example No. | Dosage, kg of active ingredient/ hectare | Herbicidal effect | | | | | |
|---|---|---|---|---|---|---|---|
| | | CYI | LOM | ECG | SIA | STM | CRS |
| 29 | 2.4 | 5 | 5 | 5 | 4 | 5 | 5 |
| 1 | 2.4 | 5 | 2 | 5 | 4 | 5 | 4 |
| 30 | 2.4 | 5 | 2 | 3 | 3 | 3 | 3 |
| 53 | 2.4 | 5 | 5 | 5 | 5 | 5 | 5 |
| 54 | 2.4 | — | 4 | 5 | 2 | 4 | 5 |
| 56 | 2.4 | 5 | 1 | 5 | 5 | 5 | 4 |
| 31 | 2.4 | 4 | 3 | 5 | 3 | 4 | 2 |
| 63 | 2.4 | — | 3 | 4 | 2 | 5 | 2 |
| 64 | 2.4 | 5 | 5 | 5 | 5 | 5 | 5 |
| 12 | 2.4 | 3 | 2 | 4 | 4 | 3 | 2 |
| 50 | 2.4 | 5 | 1 | 5 | 4 | 5 | 3 |

Abbreviations:
CYI = Cyperus iria
LDM = Lolium multiflorum
ECG = Echinochloa crus galli
SIA = Sinapis alba
STM = Stellaria media
CRS = Chrysanthemum segetum V. Herbicidal effect in rice Seeds and tubers or young plants of various rice weeds, such as, for example, species of Cyperus, Echinochloa, Eleocharis and Salvinia, are bedded out in closed pots of diameter 13 cm and are filled up with water to a height of 1 cm above the soil. The same procedure is carried out with rice plants. Using the preemergence technique, the compounds are poured into the irrigation water (in the form of aqueous suspensions or emulsions or in the form of granules) or are sprinkled into the water. 3 weeks later the herbicidal effect and the harmful effect on rice are assessed in each case. The results showed that the compounds according to the invention are suitable for combating weeds selectively in rice. Compared with the rice herbicides available hitherto, the compounds according to the invention are distinguished by the fact that they combat, in very effective and low application rates, numerous seed-propagated weeds and also weeds which germinate from long-life organs such as tubers (Cyperus) or rhizomes and are difficult to combat, and do not damage the rice at all.

TABLE V

| Compound | Dosage, kg of AS/ hectare | Rice sown | Rice planted | % damage | | | | |
|---|---|---|---|---|---|---|---|---|
| | | | | ECG | CYD | EOA | CYS | SAN |
| 1 | 2 | 0 | 0 | 100 | 100 | 100 | 100 | 100 |
| | 1 | 0 | 0 | 100 | 100 | 95 | 98 | 100 |
| | 0.5 | 0 | 0 | 99 | 100 | 92 | 90 | 95 |

The compounds according to Examples Nos. 29, 53, 54, 56 and 50 have a similar effect.

C. Fungicidal effectiveness

Example VI

Wheat plants were heavily inoculated in 3-leaf stage with conidia of powdery mildew of wheat (*Erysiphe graminis*) and were placed in a greenhouse at 20$o@C and 90-95% relative humidity. 3 days after the inoculation, the plants were treated with the compound and concentrations of active compound listed in Table I. After an incubation time of 10 days the attack of wheat mildew on the plants was investigated. The degree of infestation is expressed as % of leaf surface infested, relative to untreated, infested control plants (=100% attack). The results are summarized in Table VI.

TABLE VI

| Compound according to Example No. | % leaf area infested by powdery mildew of wheat at ... mg of active compound/ liter of spray liquor | | |
|---|---|---|---|
| | 500 | 250 | 125 |
| 67 | 0 | 0 | 0 |
| 66 | 0 | 0 | 0-3 |
| 1 | 0 | 0 | 0 |
| 31 | 0 | 0 | 0 |
| 56 | 0 | 0 | 0 |
| 63 | 0 | 0 | 0 |
| 57 | 0 | 0 | 0 |
| 54 | 0 | 0 | 0 |
| 58 | 0 | 0 | 0 |
| 50 | 0 | 0 | 0 |
| 17 | 0 | 0 | 0 |
| untreated, infested plants | | | 100 |

Example VII

Barley plants were heavily inoculated in the 3-leaf stage with conidia of powdery mildew of barley (*Erysiphe graminis* sp. *hordei*) and were placed in a greenhouse at 20° C. and 90-95% relative humidity. 3 days after inoculation the plants were treated with the compounds and concentration of active compound listed in Table VII. After an incubation time of 10 days the attack by barley mildew on the plants was investigated. The degree of infestation is expressed as % of leaf surface infested, relative to untreated, infested control plants (=100% attack). The results are summarized in Table VII.

TABLE VII

| Compound according to Example No. | % leaf area infested by powdery mildew of barley at ... mg of active compound/liter of spray liquor | | |
|---|---|---|---|
| | 500 | 250 | 125 |
| 67 | 0 | 0 | 0 |
| 1 | 0 | 0 | 0 |
| 31 | 0 | 0 | 0 |
| 56 | 0 | 0 | 0 |
| 50 | 0 | 0 | 0–3 |
| untreated, infested plants | | | 100 |

Example VIII

Cucumber plants (variety Delikatess) were heavily infested in the 2-leaf stage with a conidia suspension of powdery mildew of cucurbits (*Erysiphe cichoracearum*). After the spore suspension had dried for a period of 30 minutes, the plants were placed in a greenhouse at 22° C. and 90% relative humidity. 3 days after infestation, the plants were treated with the compounds and concentrations of active compound mentioned in Table VIII. Assessment was carried out after 10 days. The degree of infestation is expressed as % of leaf area infested, relative to untreated, infested control plants (=100% attack). The results are summarized in Table VIII.

TABLE VIII

| Compound according to Example No. | % leaf area infested by powdery mildew of cucurbits at ... mg of active compound/liter of spray liquor | | |
|---|---|---|---|
| | 500 | 250 | 125 |
| 67 | 0 | 0 | 0 |
| 1 | 0 | 0 | 0 |
| 31 | 0 | 0 | 0 |
| 56 | 0 | 0 | 0 |
| untreated, infested plants | | | 100 |

Example IX

Wheat plants were treated with the compounds and concentrations of active compound claimed in Table IX. When the coating of active compound had dried, the plants were inoculated with spores of brown rust of wheat (*Puccinia triticina*) and were placed, dripping wet, in an air-conditioned chamber at 20° C. and 100% relative humidity. 24 hours later the plants were returned to a greenhouse and were examined there, 14 days after inoculation, for attack by brown rust of wheat. The degree of infestation was expressed as % of leaf area infested, relative to untreated, infested control plants (=100% attack). Table IX shows the good effect of the compounds investigated.

TABLE IX

| Compound according to Example No. | % leaf area infested by brown rust at ... mg of active compound/liter of spray liquor | | |
|---|---|---|---|
| | 500 | 250 | 125 |
| 67 | 0 | 0 | 0 |
| 1 | 0 | 0 | 0 |

TABLE IX-continued

| Compound according to Example No. | % leaf area infested by brown rust at ... mg of active compound/liter of spray liquor | | |
|---|---|---|---|
| | 500 | 250 | 125 |
| 31 | 0 | 0 | 0 |
| 56 | 0 | 0 | 0 |
| 57 | 0 | 0 | 0 |
| 54 | 0 | 0 | 0 |
| 65 | 0 | 0 | 0 |
| 68 | 0 | 0 | 0 |
| 50 | 0 | 0 | 0 |
| 17 | 0 | 0 | 0 |
| untreated, infested plants | | | 100 |

Example X

The active compounds and concentrations claimed in Tables X and XI were added to bio-malt agar. When the agar had solidified, it was inoculated with various cultures of *Botrytis cinerea* which are sensitive or resistant to benzimidazole and dicarboximide. 20 µl of each spore suspension were applied to the center of the agar plate. The tests were evaluated 6 days after inoculation. The degree of effectiveness of the active compounds is expressed as a % compared with the control (agar medium without active compound).

TABLE X

| Compounds according to Example No. | *Botrytis cinerea*, strain sensitive to BCM and Iprodione | |
|---|---|---|
| | Degree of effectiveness as % at ... ppm of active compound | |
| | 2000 | 500 |
| 67 | 100 | 100 |
| 58 | 100 | 100 |
| 66 | 100 | 100 |
| 68 | 100 | 100 |
| 31 | 100 | 100 |
| 56 | 100 | 100 |
| 50 | 100 | 100 |
| Control | 0 | |

TABLE XI

| Compounds according to Example No. | *Botrytis cinerea*, strain resistant to BCM and Iprodione | |
|---|---|---|
| | Degree of effectiveness as % at ... ppm of active compound | |
| | 2000 | 500 |
| 67 | 100 | 100 |
| 1 | 100 | 100 |
| 58 | 100 | 100 |
| 66 | 100 | 100 |
| 68 | 100 | 100 |
| 31 | 100 | 100 |
| 56 | 100 | 100 |
| 50 | 100 | 100 |
| Control | 0 | |

We claim:
1. A compound of the formula I

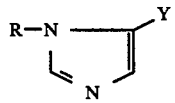

in which
R is a radical of the formulae

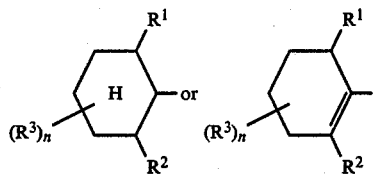

n is 0 to 6,
Y is

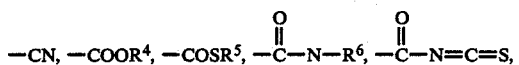

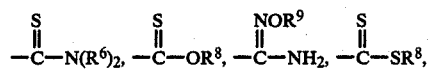

m is 1 to 4, $R^1$ and $R^2$ independently of one another are $(C_1-C_4)$-alkyl or hydrogen, $(C_1-C_4)$-alkoxy-$(C_1-C_4)$-alkyl or halogen, $R^4$ is hydrogen, $(C_1-C_{12})$-alkyl, $(C_1-C_{12})$-alkyl which is monosubstituted to trisubstituted by hydroxyl, halogen, $(C_1-C_6)$-alkoxy, $(C_1-C_4)$-alkoxy-$(C_1-C_4)$-alkoxy, $(C_1-C_4)$-alkylthio, $(C_1-C_4)$-alkylsulfinyl, $(C_1-C_4)$-alkylsulfonyl, mono-$(C_1-C_4$-alkyl)-amino, di-$(C_1-C_4$-alkyl)-amino, cyano, aminocarbonyl, $(C_1-C_4)$-alkanoyl, $(C_1-C_4$-alkoxy)-carbonyl, cyclo-$(C_3-C_7)$-alkyl, tri-$(C_1-C_4$-alkyl)silyl, benzyloxy, benzyloxyethoxy, phenyl or phenyl which is mono substituted or polysubstituted by halogen or $(C_1-C_4)$-alkyl, by phenoxy or phenylthio both of which can be monosubstituted or polysubstituted by halogen or $(C_1-C_4)$-alkyl, carboxyl, carboxylate containing a cation which can be employed in agriculture or by the radical —O—N=C(CH$_3$)$_2$; or $R^4$ denotes $(C_3-C_6)$-alkenyl, halogenated $(C_3-C_6)$-alkenyl, cyclo-$(C_3-C_7)$-alkyl which is unsubstituted or substituted by $(C_1-C_4)$-alkyl, cyclo-$(C_5-C_7)$-alkenyl, $(C_3-C_7)$alkynyl, 1,2-epoxy-prop-3-yl, phenyl which is unsubstituted or monosubstituted or disubstituted by halogen, nitro, cyano, $(C_1-C_4)$-alkyl, $(C_1-C_4$-alkoxy)-carbonyl or $(C_1-C_4)$-alkoxy; $(C_1-C_4$-alkyl)-carbonyl, phenylcarbonyl in which the phenyl ring can be substituted by halogen, nitro, cyano or $(C_1-C_4)$-alkyl, or a radical of the formulae —N=CR$^{14}$R$^{15}$, —NR$^6$R$^{16}$, $R^5$ is $(C_1-C_{12})$-alkyl or $(C_1-C_{12})$-alkyl which is not more than disubstituted by $(C_1-C_4)$-alkoxy-ethoxy, cyclo-$(C_3-C_6)$-alkyl, benzyloxy, phenyl, phenoxy, $(C_1-C_4)$-alkylthio, $(C_1-C_4$-alkoxy)-carbonyl, carboxyl or carboxylate containing a cation which can be employed in agriculture, the $R^6$s independently of one another each are hydrogen, $(C_1-C_6)$-alkyl, phenyl or $(C_3-C_6)$-alkenyl, $R^7$ is hydrogen, $(C_1-C_{12})$-alkyl or $(C_1-C_{12})$-alkyl which is not more than disubstituted by $(C_1-C_6)$alkoxy, $(C_1-C_4)$-alkoxyethoxy, hydroxyl, halogen cyclo-$(C_3-C_6)$-alkyl, benzyloxy, cyano, aminocarbonyl, carboxyl, $(C_1-C_4$-alkoxy)-carbonyl, formyl, phenyl or phenoxy; phenyl or phenyl which is not more than disubstituted by halogen, nitro, cyano, $(C_1-C_4)$-alkyl or $(C_1-C_4)$-alkoxy; $(C_3-C_6)$alkenyl, $(C_3-C_6)$-cycloalkyl or a radical of the formulae —NR$^6$R$^{17}$, —OR$^9$, —NH—CO—NH$_2$, —NH—C-S—NH$_2$ or —SO$_2$R$^{18}$, or $R^8$ is H, $(C_1-C_6)$-alkyl or phenyl or, in the event that R=—CS—OR$^9$, is a cation which can be employed in agriculture, the $R^9$s independently of one another each are H, $(C_1-C_4)$-alkyl or benzyl, the $R^{14}$s and $R^{15}$s independently of one another are H or $(C_1-C_6$-alkyl which is unsubstituted or substituted by $(C_1-C_4)$-alkoxy; cyclo-$(C_3-C_6)$-alkyl, $(C_3-C_6)$-alkenyl, phenyl or benzyl or $R^{14}$ and $R^{15}$, together with the carbon atom to which they are attached, are cyclo-$(C_5-C_7)$-alkyl which is unsubstituted or substituted by methyl or halogen, $R^{16}$ is $(C_1-C_4)$-alkyl, phenyl, $(C_1-C_6$-alkyl)-carbonyl, benzyl, benzoyl, halogenobenzyl, halogenobenzoyl or methylbenzoyl, $R^{17}$ is H, $(C_1-C_4)$-alkyl, formyl, $(C_1-C_6$-alkyl)-carbonyl, benzoyl, halogenobenzoyl, methylbenzoyl or trihalogenoacetyl and $R^{18}$ is $(C_1-C_4)$-alkyl, phenyl or methylphenyl, and to salts and quaternization products thereof which are compatible for agricultural purposes.

2. The compound according to claim 1, wherein R is

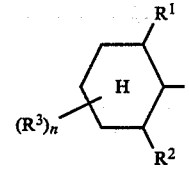

R', $R^2$ and $R^3$ are defined as in claim 1,
n is 0 or 1,
Y is —COOR$^4$.

3. A herbicidal having an effective content of a compound of the formula (I) of claim 1 and an agriculturally acceptable carrier.

4. A process for regulating the growth of plants and for combating weeds and harmful fungi, which comprises applying an effective amount of a compound of the formula (I) of claim 1 to the plants or to the cultivated area.

* * * * *